United States Patent
Wellnhofer (10) Patent No.: US 6,290,652 B1
(45) Date of Patent: Sep. 18, 2001

(54) CORRECTION OF BLOOD PRESSURE MEASUREMENTS IN INVASIVE LIQUID-FILLED SYSTEMS

(75) Inventor: Ernst Wellnhofer, Berlin (DE)

(73) Assignee: Deutsches Herzzentrum Berlin, Berlin (DE)

( * ) Notice: Subject to any disclaimer, the term of this patent is extended or adjusted under 35 U.S.C. 154(b) by 0 days.

(21) Appl. No.: 09/554,830

(22) PCT Filed: Nov. 20, 1998

(86) PCT No.: PCT/DE98/03486

§ 371 Date: May 19, 2000

§ 102(e) Date: May 19, 2000

(87) PCT Pub. No.: WO99/26531

PCT Pub. Date: Jun. 3, 1999

(30) Foreign Application Priority Data

Nov. 21, 1997 (DE) .............................................. 197 53 183
May 4, 1998 (DE) .............................................. 198 20 811

(51) Int. Cl.$^7$ ........................................................ A61B 5/02
(52) U.S. Cl. ........................... 600/486; 600/487; 600/505
(58) Field of Search ........................... 600/481, 485–488, 600/500–505

(56) References Cited

U.S. PATENT DOCUMENTS

| 4,232,373 | 11/1980 | Jackson et al. | 364/572 |
|---|---|---|---|
| 5,065,765 | * 11/1991 | Eckerle et al. | 600/485 |
| 5,333,614 | * 8/1994 | Feiring | 600/466 |

FOREIGN PATENT DOCUMENTS

| 39 27 990 A1 | 2/1991 | (DE) . |
|---|---|---|
| WO 90/11043 | 10/1990 | (WO) . |
| WO 96/04842 A1 | 2/1996 | (WO) . |

OTHER PUBLICATIONS

S. Lohmann et al., "Characterization of laser–induced pressure transients by means of piezoelectric PVDF–films", pp. 1–10, ECS/SPIE CCDE, SPIE Manuscript Sheet, No. 262414.

* cited by examiner

Primary Examiner—Angela D. Sykes
Assistant Examiner—Ryan Carter
(74) Attorney, Agent, or Firm—Christie, Parker & Hale, LLP

(57) ABSTRACT

The invention relates to a method for the correction of measured value falsifications in invasive pressure measurements with a fluid-filled system, in which the measured pressure is passed via the fluid-filled system to an external pressure transducer, which converts the pressure signal into an electrical signal. To provide a method and a device for invasive pressure measurement with fluid-filled systems which are improved with respect to the correction of measured value falsifications, are cost-effective and versatile in their use, the electrical signal is passed through an analog/digital converter and the digitized signal is fed to a signal analyzing and processing unit, which operates on the basis of a digital Fourier analysis. Furthermore, a heartbeat-related or segmental analysis is carried out and the signal is combined with empirically determined correction data on the basis of the analysis. The correction data are emitted as Fourier coefficients and the signal corrected by the signal analyzing and processing unit is passed to an output and/or evaluating unit.

49 Claims, 3 Drawing Sheets

CORRECTION OF BLOOD PRESSURE MEASUREMENTS IN INVASIVE LIQUID-FILLED SYSTEMS

BACKGROUND

The invention relates to a method and a device for the correction of measured value falsifications in invasive pressure measurements with a fluid-filled system, in which the measured pressure is passed via the fluid-filled system to an external pressure transducer, which converts the pressure signal into an electrical signal.

Fluid-filled systems have been used for decades in connection with invasive pressure measurement for intravenous and intraarterial pressure measurement. Such systems, also referred to as catheters, are frequently used in invasive cardiology, intensive medicine and in anesthesia, where they are used for exact pressure measurement. Use is particularly appropriate for impedance measurements on the arterial system of vessels or for derivatives of pressure with respect to time (dp/dt) for measuring the isovolumetric force of contraction or relaxation disorders of the ventricles. For this purpose, it must be possible to analyze resonances of the original pressure signals of up to approximately 30 Hz faithfully with respect to the original, that is faithfully with respect to phase and amplitude.

In invasive catheter diagnosis, the pressure measurement at a specific location in the circulation takes place via a fluid-filled system with a pressure transducer applied externally (i.e. outside the patient's body). Depending on the length, cross section, setup and elastic material properties of these systems, different resonances, attenuations and energy losses of the input pressure signal occur at the tip of the catheter.

U.S. Pat. No. 4,232,373 discloses a correction method for measurement data of a fluid-filled cardiac catheter, in which the periodically recorded signal is converted into an electrical signal, digitized and branched. Part of the signal is first passed to a correction unit and subsequently passed to a filter, while the other part is passed to the filter in an uncorrected form and with a delay. In the filter, the two parts of the signal are brought together and the corrected signal is output.

In the manuscript "Characterization of laser-induced pressure transients by means of piezoelectric PVDF-films" by S. Lohmann et al; Proc.SPIE 2624; 83–92; (1995), there is described, inter alia, the correction of laser-induced pressure waves in piezoelectric films. In this case, a description is given of the correction of a voltage signal emitted by the film by means of a Fourier transformation, in which the signal is transformed into the frequency domain and is corrected in the frequency domain by means of a correction value calculated in an algorithm. Subsequently, an inverse transformation into the time domain is carried out.

To avoid falsifications along the transmission path, the pressure transducer has been integrated into the tip of the catheter and the converted signal led out of the body via an electric line. This solution is known as a tip pressure sensor catheter. A disadvantage of this form of pressure measurement is that tip pressure sensor catheters are very expensive and have only a very restricted range of variations with respect to shape and size. Therefore, it has only been possible for this solution to be established in the scientific sector to a limited extent.

A further possible way of compensating for measured value falsifications is to consider the system as a simple forced oscillation in the physical sense and to carry out a correction of the transmission function of the system of the 2nd order after determination of the resonant frequency and the attenuation coefficient by means of an analog electric circuit or a corresponding numerical algorithm. The disadvantages of this approach are that the consideration as a system of the 2nd order is a great simplification of the actual physics of the system, in which multiple resonances can occur particularly in the case of relatively complex systems. The transmission function is, in principle, to be newly determined for each actual system, even when there are customary and frequent changes such as exchanging the catheter in the system, it being problematical to determine the transmission function by means of a flushing test or square-wave test on the patient. The transmission function is, furthermore, dependent on the elasticity of the system and this in turn is dependent on the filling pressure, the gases dissolved in the fluid and material properties of the system. Finally, these systems are very complicated to operate.

A further procedure introduced on the market is the use of systems which have been specially configured and optimized in terms of fluid mechanics by in-vitro test studies and which comprise a pressure transducer, a tube, a three-way cock, an array of cocks, a catheter and possibly an attenuator. A disadvantage of this method is that the test effort is very great and that, in invasive cardiology, an extremely wide variety of systems are used, limiting the use of this method. Furthermore, it is not possible for this attenuation to be switched off to exclude an attenuation by blood or air in the system. What the catheter personnel are accustomed to seeing makes them associate attenuation with an inadequately flushed system and they would easily misinterpret such an attenuated system.

The object of the present invention is to provide a method and a device for invasive pressure measurement with fluid-filled systems which are improved with respect to the correction of measured value falsifications, are cost-effective and versatile in their use.

SUMMARY

The method according to the invention allows a correction of the pressure profile that is faithful with respect to phase and amplitude by the evaluation and processing of the signal by means of digital Fourier analysis, without using Fourier transformation of a signal of a fixed length but instead working with variable signal lengths. In this way, the optimum segment length, with which a minimal error occurs, can be determined for the subsequent correction.

The correction method can be used for a wide variety of systems, thereby reducing the expenditure in financial terms and in terms of apparatus for invasive pressure measurements. Furthermore, there are no longer any type-dependent restrictions, so that the systems or catheters that are optimum for the patient can be used, without having to dispense with corresponding accuracy.

The output on various evaluating or indicating units permits rapid and comprehensive evaluation of the data. A correction of the signals is possible both online and offline.

For determining the segment length of the signal to be corrected, a comparison of the deviation of the inverse transform from the original signal is carried out on the basis of the variation of the length of a base signal. Starting from a prescribed base signal length, a comparison of the inverse transform of the base signal with the original signal is carried out. In this comparison, a deviation or error which changes in dependence on the chosen signal length is established. The signal length is then increased or reduced in steps, depending on which base signal length was taken as a starting point. If the error reaches a prescribed value, i.e. if a specific accuracy is achieved, the variation of the segment length is discontinued in order to reduce the computational effort. An optimum segment length is found when the minimum of the deviation of the inverse transform from the original signal has been determined.

It has been found to be favorable to start out in the variation of the base signal length from a minimum length, which is increased in steps. If the deviation is reduced when the segment length is increased, the transformation routine with error determination is repeated until the prescribed value for the deviation or the minimum is reached. The segment length or curve length found in this way is optimum for the Fourier transformation of the correction method, since the measured signal can be broken down virtually completely into harmonic oscillations and the error is minimal. A value which is less than the length of a heartbeat is to be assumed as the minimum length. A minimum signal length of 0.3 seconds has been found to be a favorable value.

For faster determination of the optimum or prescribed value, the step size of the change in segment length change is varied in proportion to the deviation of the inverse transform from the original signal. With a small error, a correspondingly small change is made, since the segment length is already close to the optimum and the highest possible resolution is aimed for by a small step size. With a large error, the same applies in a correspondingly converse sense.

A variant of the method according to the invention allows a correction of the pressure profile that is faithful with respect to phase and amplitude by the heartbeat-related evaluation and processing of the signal by means of digital Fourier analysis. Other correction methods are only inadequately able to take into account the different frequencies of the heartbeats.

In an advantageous refinement of the invention, the correction data determined on the basis of reference pressure measurements are called up from a matrix of correction data records, making a large number of data records available quickly and easily. To keep the number of empirically determined correction data records to a commercially acceptable order of magnitude, if the exactly matching data record is missing an interpolation is carried out between the closest data records.

To obtain a signal that is corrected as accurately as possible, a phase correction and amplitude correction are provided, it having proven to be advantageous to carry out a phase correction of the signal only at the points where that signal has an amplitude.

For determining the correction data records, in one embodiment of the invention the catheter tip is introduced into a device which can be subjected to pressure and this device is subjected to different medium pressures and frequencies. In separate measurements, the medium pressure is varied in defined equidistant step sizes and the lowest frequency (fundamental frequency) of the frequency spectrum is likewise varied in defined equidistant step sizes. These settings produce a medium pressure/frequency grid of coordinates, which represents the basis for the correction data record matrix. As an alternative to this, the transmission characteristic is determined by means of a white frequency noise and the correction takes place by means of deconvolution of the output signal with the transmission function. A reference pressure measurement takes place with another measuring system, preferably with a tip pressure sensor catheter.

It has been found to be favorable with respect to the computational effort and correction results for a defined signal in the form of a frequency grid to be used for determining the correction data records for the system excitation. On the basis of a fundamental oscillation, which for computational reasons advantageously lies in the range between 0.1 and 1 Hz, the system is excited with equidistant harmonic oscillations. From a fixed upper limit, the number of excitation frequencies required is consequently obtained. 40 Hz has been found to be a physiologically appropriate upper limit for the excitation frequency.

In separate measurements, the medium pressure is varied in defined equidistant step sizes. These settings provide a set of correction data records for various medium pressures. A reference pressure measurement takes place, as before, with another measuring system.

To achieve a coincidence of the spectral lines of the signal to be corrected with those of the correction data record vector, the pressure signal segment is multiplied repeatedly until a ratio corresponding to the resolution of the correction data record is obtained between the sampling rate and the length of the curve segment. If it does not correspond to the resolution, the next-smaller ratio between the sampling rate and the length of the curve segment is expediently set and the assignment to the spectral lines of the correction data record takes place by rounding up to the next corresponding line.

Since a pressure transducer generally does not emit an adequately strong signal, an amplifier is provided between the pressure transducer and the analog/digital converter. The pressure transducer is activated and supplied with the required operating voltage by means of a supply line of the signal processing and analyzing unit.

For the correction of the recorded signals in the heartbeat-related analysis, it is very important that the length of the heartbeat is known, since only in this way can a beat be processed exactly. The length of the beat is advantageously calculated by means of an autocorrelation function and its first derivative with respect to time. A prefiltering with a low-pass filter with a high cut-off frequency of 30–40 Hz is optionally provided in order to eliminate possible interferences of the alternating current system.

For a reliable correction of the signals, it is necessary that the signal analyzing and processing unit correctly assigns the respective correction data records. Since the various systems are differently designed, have different resonant frequencies and can be changed considerably by built-on parts, a system identification is carried out by means of a test signal response before the measured value is recorded. A defined signal is preferably transmitted from a reference pressure transmitter (calibrator) at the tip of the catheter in the direction of the pressure transducer and the system response is compared with experimentally found system responses. In this way, a classification can be performed and information obtained on which system is concerned or which correction data records are suitable for the system concerned. It is also conceivable for a signal to be transmitted from the pressure transducer in the direction of the catheter tip and the signal response to be compared with experimentally found system responses.

It has proven to be advantageous in the heartbeat-related analysis for the fundamental frequency to be determined by means of a combination of a distribution analysis of maxima of autocorrelation functions of varying length with the analysis of the minima and maxima of the curve. In online determination of the fundamental frequency specifically, it is expedient to repeat the autocorrelation function with an increasing length and to collect all the first maxima of the autocorrelation functions of the increasing length. The most frequently occurring maximum is subsequently determined by means of a distribution analysis.

A cross-correlation of the pressure signal and patient's ECG is advantageously carried out to determine the length of the fluid-filled system, i.e. the signal delay time. In a variant, the system identification is carried out automatically.

In addition to a classification of the catheter and tube system, an identification of the various pressure transducers and corresponding consideration in the selection of the correction data records is advantageously envisaged. Since the respective pressure transducers convert the pressure signals differently, on a type- or model-dependent basis, different operating voltages are required and have to be individually activated, such an adaptation is advantageous in order to keep the measured value falsification as low as possible and to carry out a correct activation.

As an additional check and in order to make use of the operator's experience, a manual interaction is envisaged in the system identification, so that a selection or input can be performed in addition to or as a departure from the option calculated.

The system transmission properties of the fluid-filled system correlate with the elasticity of the catheter and line system. Depending on the material properties, a different initial stress due to the average internal pressure prevailing in the system may therefore change the system transmission properties significantly. Continuous measurement of the medium pressure is therefore part of the automatic signal analysis. The selection of the correction data records takes place according to the medium pressure.

For a reliable correction of the pressure signal it is advantageous if so-called artifacts are detected. This takes place on the basis of the system identification determined. Excessive deviations are detected and disregarded. In a variant of the method, in addition to the correction of the pressure signal, an artifact identification and elimination is carried out by means of brief autocorrelation. In the autocorrelation function, interference spikes in the pressure profile can be automatically detected and localized. An interpolation of the curve at the point of the spike eliminates the interference.

In addition to the correction instruments described, if appropriate, a shape analysis of the pressure signal may be carried out, taking higher harmonic fundamental oscillations into account, so that a correspondingly refined method is available for compiling and selecting the correction data records.

In a further refinement of the invention, an optional output of the untransformed signal is envisaged, enabling the operator to detect the mechanical attenuation due to blood clots or small air bubbles.

Static calibrating options which simplify operation, or supply more easily comparable results or signal profiles, are expediently provided. By zero point calibration, the measured pressure is assumed as the zero point and serves as a basis for the pressure monitoring system, which indicates the signals. In this way, indications which can be compared with one another become possible without, for example, blood pressure fluctuations and system-related offsets between different measurements having to be taken into account. For checking the connection between the signal analyzing and processing unit and the pressure monitoring system and for checking the calibration, a reference pressure (for example 100 mmHg, which can be set in the instrument menu) can be sent to the pressure monitoring system. In analogy with the reference pressure, various stored pressure curves may be sent as a test signal to the pressure monitoring system.

In a further embodiment of the invention, the signal is post-filtered or post-corrected, in order to remove interference signals and to have a signal profile that is as unfalsified as possible. Such a post-correction is preferably carried out with respect to time on the basis of the first derivative of the corrected and possibly smoothed pressure signal. For post-filtering, frequency or mean-value filters are suitable.

In an advantageous refinement of the invention, an automatic adaptation to changes of the resonant response of the system as a result of pressure changes is carried out. The changes in blood pressure may be caused, for example, by circulation-related reactions or medicaments, the changes in the resonant response being of a system-specific nature. The corresponding variables are determined continuously and are continuously fed to the signal analyzing and processing unit, which takes the changes into account in the selection of the correction data records.

A device according to the invention for carrying out the method has a fluid-filled system for invasive pressure recording and a pressure transducer, which converts the pressure pulses into electrical signals. Connected thereto is a recording unit for the original voltage signals of the pressure transducer and analog/digital converter, which prepares the signal for digital processing. In the signal analyzing and processing unit, which is designed for example as a computer, the individual data records are provided with correction factors in dependence on the system parameters, on the basis of a digital Fourier analysis, and are fed to an interface. The output unit processes the corresponding signals, for example as an analog signal, as a digital signal, as a printout or as a display on a monitor.

The interface advantageously has a digital/analog converter, amplifiers and/or an adaptor, so that the corrected signal can be fed to a monitoring system, and can be transmitted to a computer in an amplified form and/or remaining in a digitized form.

A correction data record matrix, which contains correction factors determined from experimental reference pressure measurements, is advantageously stored in a memory of the signal analyzing and processing unit. In connection with the corresponding data processing programs, the respective or interpolated correction vectors can then be selected, interpolated if appropriate and combined with the digitized pressure signal.

An attenuation is normally associated with an inadequately flushed system. To make use of previous experience, the device advantageously has a signal output for the uncompensated signal, in order that the operator has the possibility of comparing the corrected pressure signals with the signals in pure form and in this way has a check on the correction method.

To take blood pressure fluctuations into account in the correction method, in a development of the invention a device for their measurement is provided, the measured values determined having an influence on the selection of the correction data record.

BRIEF DESCRIPTION OF THE DRAWINGS

The invention is explained in more detail below on the basis of exemplary embodiments represented in the drawing, in which.

DETAILED DESCRIPTION

Figure 1:
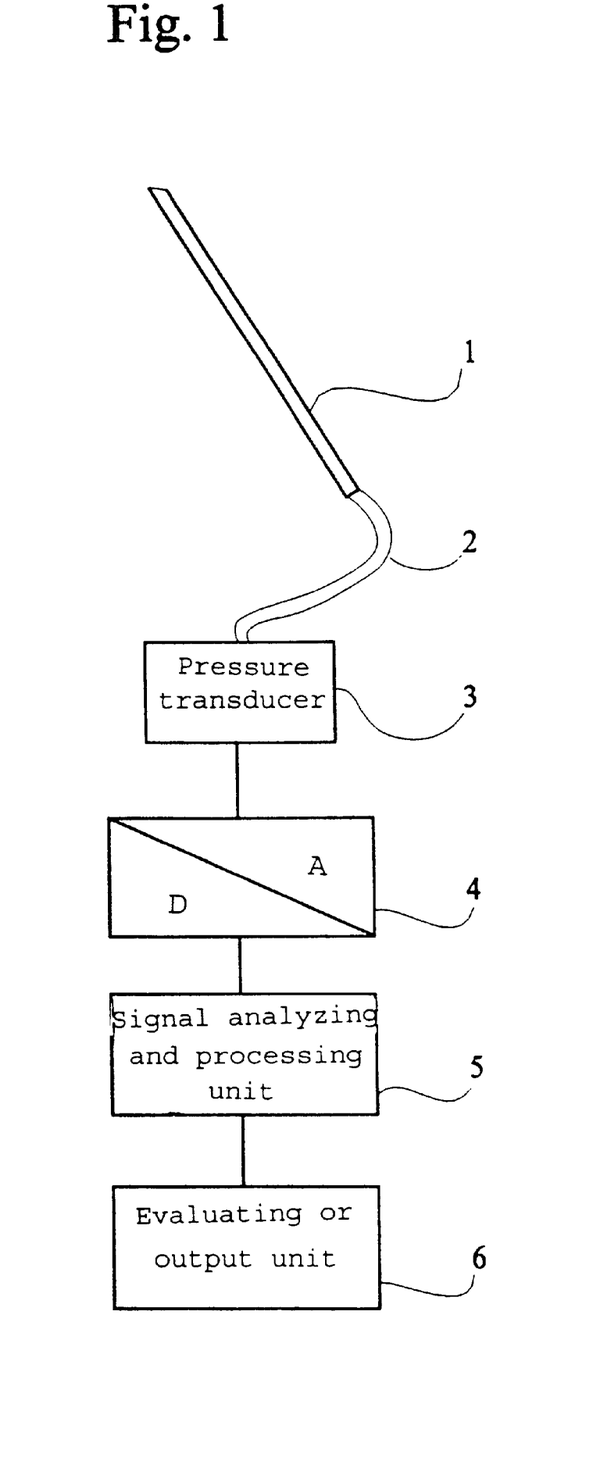
FIG. 1 shows a basic setup for the measured value correction.

FIG. 1 shows a basic setup of an invasive pressure measurement by means of a fluid-filled system. In this arrangement, a so-called catheter 1 is moved through the arterial or venous system of a patient into the proximity of the point at which the pressure is to be measured. For the patient to be influenced as little as possible by the catheter 1, the latter has the smallest possible dimensions. The catheter 1 itself consists of an elastic material and is of a tubular design. At the tip of the fluid-filled catheter 1 there is an opening, through which pressure pulses are recorded and passed on through the catheter 1 and a likewise fluid-filled line 2 to a pressure transducer 3.

In dependence on the pressure pulses, the pressure transducer 3 generates electrical signals, which can be correspondingly displayed or evaluated. This method has long been known in principle. A possible correction of the transmission function of this system of the second order takes place after determining the resonant frequency and the attenuation coefficient by means of an analog electric circuit or a corresponding numerical algorithm.

For effective correction of the measurement falsifications occurring during use of the method described above, which lie in the range of up to 40%, in the method according to the invention there is arranged between the pressure transducer 3 and the signal analyzing and processing unit 5 an analog/digital converter 4, which converts the analog signals of the pressure transducer 3 into digital signals, which are applied to the input of the signal analyzing and processing unit 5. Within the signal analyzing and processing unit 5, the measured data are subjected to correction factors on the basis of a digital Fourier analysis and are passed on to the output or evaluating device 6.

Before the correction of the signals, an overall system identification of the mechanical part of the system is carried out. Firstly, a manual or automatic identification of the connected pressure transducer 3 takes place. Subsequently, a test signal in the form of a pressure pulse, preferably generated by a calibrator, is transmitted. As an alternative, the pulse generation is performed by a pressure transducer 3. The parameters of the catheter-line system are determined from the signal response and a selection of the correction data records takes place on the basis of said parameters. Since, with the large number of components used in invasive pressure measurement and the large number of parameters, an exactly matching correction data record is not always available, the values required are determined from the existing data records by means of interpolation methods and are provided for the correction.

The signals which have been digitized and subjected to corrected Fourier coefficients are transmitted from the signal analyzing and processing unit 5 to an indicating or evaluating unit 6, it being possible for an indication to take place both on a monitor system and on a printout. Depending on the standard of the monitor, the signals are firstly fed to a digital/analog converter and subsequently output or transferred directly to a monitor which can process digital signal. If appropriate, the signals still have to be prepared in such a way as to provide a format suitable for display.

Another possibility is for the data to be transmitted to a computer, which stores and evaluates them. In this case, the data are not processed in a digital/analog converter but are passed on directly from correction.

There is also the possibility of not carrying out the correction online but of storing the data and evaluating or correcting them at a later point in time. A precondition for this is the presence of the system-specific data and the information on the measuring conditions, in order that a correct selection of the correction data records can subsequently take place. For this purpose, the data are advantageously recorded directly after the pressure transducer 3 and stored on a suitable storage medium, for example a CD or floppy disk.

In a variant of the invention, an output capability for the uncorrected signal is provided, in order that there is the possibility of comparing the corrected signals with the uncorrected signals. This has the effect on the one hand that what the operator is accustomed to seeing is not completely changed, and on the other hand that a check of the correction method takes place. For example, the presence of air bubbles in the fluid-filled system can be detected from the uncorrected signal by trained operators, so that corresponding measures can be taken. The branching of the signal may take place both before and after the analog/digital converter 4, it being expedient for an amplifier to be arranged upstream, in order that an adequately strong signal is available.

Before the actual measurement, a calibration of the pressure to be measured with respect to atmospheric pressure is usually carried out, with a three-way cock that is usually provided on the pressure transducer being actuated. Provided on the signal analyzing and processing unit 5 is an actuating element, with the actuation of which the pressure to be measured is assumed as the zero point and serves as a basis for further measurement and output.

For checking the connection between the signal analyzing and processing unit 5 and the output unit 6 and for checking the calibration, a reference pressure signal or various stored pressure curves are sent to the output unit 6. The deviation and the compensation to be carried out can be determined from the difference between the setpoint signal and the actual-value signal. If the entire measuring chain is to be checked, a reference pressure signal may be connected instead of a patient's pressure signal and, if appropriate, necessary offset and linearity corrections can be carried out at the signal analyzing and processing unit 5 for each channel.

Figure 2:
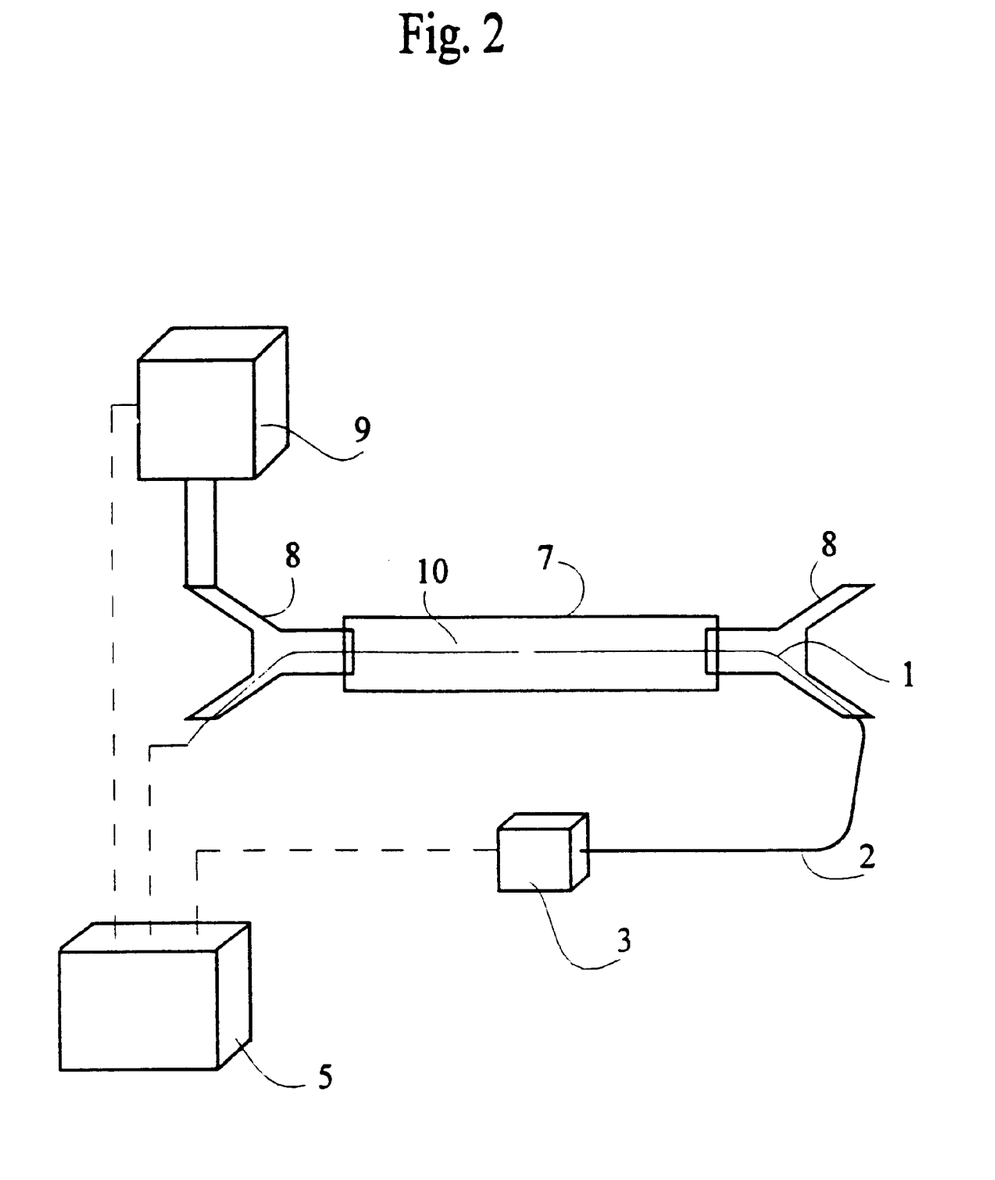
FIG. 2 shows a basic setup for the compilation of the correction data record and FIG. 3 shows a representation for determining the fundamental period.

A basic setup for the empirical determination of the correction data records is represented in FIG. 2. For determining the natural dynamics of a system, and consequently the correction data records, a tube 7 that is filled with fluid and vented is used. At the tube 7 there are respective connections 8 for filling, venting, the reference pressure measurement by means of a tip pressure sensor catheter 10 and the introduction of the catheter (test system) as well as a device for pressure generation 9 (Biotek).

After introducing the tip of the catheter 1 into the proximity of the reference pressure measurement, the tube 7 is excited by a defined frequency spectrum pressure. In separate measurements, the medium pressure, usually in the range from 0 mmHg to 130 mmHg, is varied in defined equidistant step sizes. The frequency content of the excitation signal is composed of a fundamental oscillation and a number of harmonic oscillations. The fundamental oscillation is usually 0.25 Hz and 160 harmonic oscillations are excited, so that an upper frequency of 40 Hz is achieved by the equidistant intervals. It goes without saying that other frequencies of the fundamental oscillation are possible, and in the same way the number of harmonic oscillations can be varied. However, the values mentioned represent an appropriate selection.

The Fourier spectrum of the reference signal and of the fluid pressure signal is calculated from each measurement by means of Fourier transformation. The correction data record vector is then obtained from the complex division of each spectral line of the reference pressure by the corresponding spectral line of the fluid pressure. The result is a unitless, complex correction factor for each spectral line of this measurement. All the measurements together produce the correction data record matrix for the system investigated, which are stored in the signal analyzing and processing unit 5.

In the heartbeat-related analysis, the length of the fundamental oscillation in the invasive pressure measurement corresponds to a heartbeat, it being possible for the heart rate to change considerably from beat to beat. A continuous analysis of the fundamental frequency is therefore part of the automatic signal analysis and is determined by an autocorrelation function.

In the segmental analysis of the signals recorded, different segment lengths are used, obtained from a comparison of the inverse transform with the original signal, with the segment lengths expediently being chosen such that there is a minimal error, which according to experience lies around 1%. This means that a segment length that is optimal for the correction method has been determined.

The number of Fourier coefficients, and consequently the correction data record, are consequently dependent on the length of the analyzed segment or the fundamental frequency.

In addition to the determination of the fundamental frequency or the segment length, the medium pressure is a variable to be determined. The system transmission properties of the fluid-filled system are dependent, inter alia, on the elasticity of the catheter and line system 1, 2. Depending on the material properties, a different initial stress due to the average internal pressure prevailing in the system can therefore change the system transmission properties significantly. A continuous measurement of the medium pressure is therefore likewise part of the automatic signal analysis. The selection of the correction data records takes place according to the medium pressure.

Before the beginning of the actual correction, the signal may be frequency-filtered, optional use being envisaged for the numerical filter, as well as a variation of the filter cut-off frequency, which according to experience lies between 40 and 100 Hz. Such filtering may be necessary, for example, in the event of interferences caused by the 50 Hz alternating current system.

To characterize the signal for the correction, the fundamental frequency or the segment length and the medium pressure are required.

Figure 3:
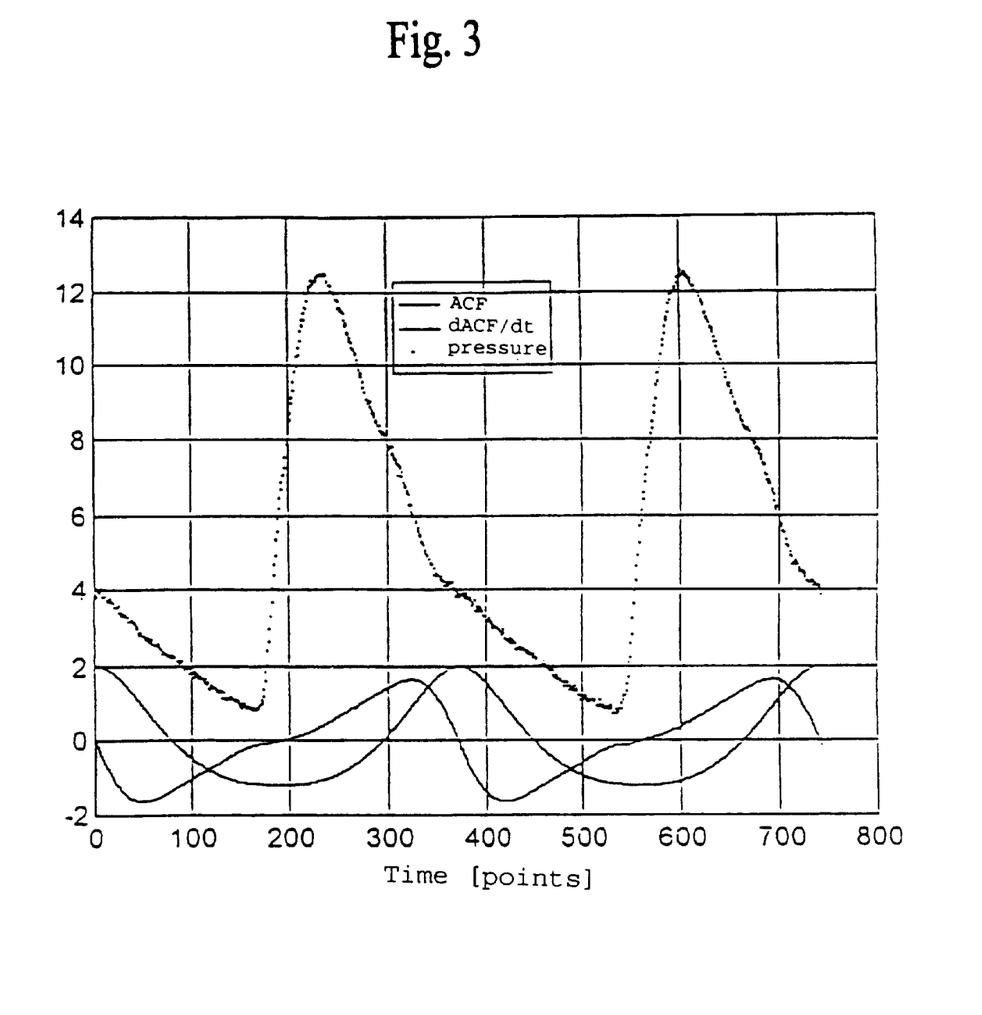

An example of the determining of the fundamental period is represented in FIG. 3. For this purpose, firstly the autocorrelation function (ACF) is calculated. The time until the occurrence of a main maximum exceeding a threshold value is the fundamental period.

On the basis of the level of the medium pressure, the corresponding correction data record is selected. The medium pressure is obtained from the normalized level of the first spectral line (line of the frequency zero, direct component) of the Fourier transform of the signal.

In addition, a possible dependence of the transmission characteristic of the system on the frequency content of the exciting signal is countered by a simple shape analysis of the signal, based on higher harmonic fundamental oscillations with corresponding modification of the correction data records.

In a preferred alternative, the complex Fourier coefficients of the pressure signal are then multiplied by the complex correction coefficients of the selected correction factor. In a way similar to in the compilation of the correction data records, in the heartbeat-related analysis it is also the case for the pressure signal that the fundamental frequency and its harmonic oscillations are corrected only where they exceed a threshold value, up to an upper frequency corresponding to the highest frequency of the correction data records, in the present case 40 Hz. All other frequency components are set to zero.

The multiplication produces the corrected Fourier spectrum of the pressure signal, that is then inversely transformed into the corrected pressure signal by means of inverse discrete Fourier transformation.

In another embodiment of the invention, in the heartbeat-related analysis the variables of fundamental frequency and medium pressure are used for selecting the corresponding correction data record from the correction data record matrix. If the position of the measurement does not lie exactly at a coordinate point of the matrix, all the coefficients are newly calculated with a weighted interpolation from the neighboring coefficients.

The reciprocal value of the fundamental frequency, the fundamental period, determines the number of points for the subsequent discrete Fourier transformation of the pressure signal, the segment to be corrected being doubled or multiplied as required for the Fourier analysis. The complex Fourier coefficients of the pressure signal are then multiplied by the complex correction coefficients of the selected or interpolated correction vector.

To achieve a coincidence of the spectral lines of the pressure signal to be corrected with those of the correction data record vector, the pressure signal segment (here a heartbeat) is multiplied repeatedly until the ratio which corresponds to the resolution of the correction data record is obtained between the sampling rate and the length of the curve segment.

If, for example, correction coefficients for the frequencies of 0.25 Hz, 0.50 Hz, 0.75 Hz, . . . 40 Hz (spectral resolution of 0.25 Hz) are present, at a sampling rate of 1000 Hz the curve segment of the pressure signal must contain at least 4000 points, since then a ratio of the sampling rate to the length of the curve segment of ¼ is obtained (<=>0.25 Hz). If this ratio cannot be exactly achieved, the next-smaller ratio (<¼) is set. The assignment to the spectral lines of the correction data record then takes place by a rounding up to the next corresponding line.

For determining the fundamental frequency, a distribution analysis of maxima of autocorrelation functions of varying length is combined with the analysis of the minima and maxima of the curve.

In the method for the online determination of the fundamental frequency of a pressure signal, the fundamental frequency is calculated by means of an autocorrelation function (ACF). In this case, the number of function values up to the first main maximum corresponds to the length of the heartbeat, in other words the reciprocal value of the fundamental frequency. Since, in online operation, the number of measured values is small at the beginning and increases with time, the ACF is repeated with an increasing length. This gives rise to the problem that a considerably changed second heartbeat strongly influences the result. For the optimum decision as to when the length of the heartbeat has been correctly determined, all the first maxima of the ACFs of increasing length are collected and the maximum which occurs most frequently is selected by means of a distribution analysis.

In a segmental analysis of the measured signal it is possible to dispense with a determination of the fundamental frequency by means of autocorrelation. For determining the segment length, the complex Fourier spectrum is calculated for a minimum length, for example 0.3 seconds, of the digitized pressure signal. The frequency components above a fixed limit, which is determined by the highest frequency of the correction data records, in the present case 40 Hz, are set to zero. Subsequently, the spectrum is transformed back into the time domain and compared point by point with the original curve. The comparison gives a deviation with a specific value. The length of the investigated segment is then increased in steps and the transformation, the frequency filtering, inverse transformation and deviation determination are repeated until a minimum of the deviation has been found. The segment length determined in this way is optimal for the Fourier transformation of the correction method, that follows the segment length determination.

A signal sampled at 1000 points per second for the correction data record is treated with a 4000-point Fourier transformation. This gives:

$$f_1=0 \text{ Hz}, f_2=0.5 \text{ Hz, etc. up to } f_n=40 \text{ Hz}$$

If the curve segment to be corrected is likewise sampled at 1000 points per second and the fundamental period is 1000 points long, the frequencies of the Fourier transformation are obtained as:

$$h_1=0 \text{ Hz}, h_2=1 \text{ Hz}, h_3=2 \text{ Hz etc. up to } h_m=999 \text{ Hz}$$

To be able to apply the 160 points of the Fourier transformation of the correction data record to the 1000 points of the curve segment while retaining a steadily progressing pressure profile, the corresponding frequency lines up to 40 Hz are used for the correction and are multiplied by the values of the curve segment. All the other frequency lines are set to zero. The multiplication produces the corrected Fourier spectrum of the pressure signal, which is then inversely transformed into the corrected pressure signal by means of inverse discrete Fourier transformation.

For post-processing operations, as in the case of the signal input, the output signal can likewise be frequency-filtered. The numerical filter may be optionally switched on and off by the user and the filter cut-off frequency can be varied. A signal improvement is also achieved by a mean-value filtering connected to the frequency filtering, for which a freely configurable mean-value filter (moving average filter) with a length of 2 to 20 points is provided. These filters can also be switched on and off. To improve the correction result, an additional correction may be switched on, which adds or subtracts to or from the corrected signal, on a point-by-point basis, the first derivative with respect to time, displaced by n points.

What is claimed is:

1. A method for the correction of measured value falsifications in invasive pressure measurements with a fluid-filled system, the method comprising:

passing measured pressure, as a pressure signal, via the fluid-filled system to an external pressure transducer;

converting the pressure signal; into an electrical signal digitizing the electrical signal in an analog/digital converter;

feeding the digitized signal to a signal analyzing and processing unit, which operates on the basis of a Fourier analysis;

analyzing the digitized signal in segments;

combining the analyzed signal with prescribable correction data in the form of Fourier coefficients, the analyzed signal being at least one segment of the digitized signal;

varying length of the segments, such that a minimal error occurs in the Fourier analysis and the digitized signal is corrected by the signal analyzing and processing unit; and passing the corrected signal to at least one of an output and evaluating unit.

2. The method according to claim 1 wherein the length of the segments is determined by a variation of length of a base signal and a comparison of an inverse transform of the base signal with the electrical signal, deviation of the inverse transform of the base signal from the electrical signal assuming a prescribed value.

3. The method according to claim 2 wherein the length of the segments is determined by a minimum of the deviation of the inverse transform of the base signal from the electrical signal.

4. The method according to claim 2 or 3 wherein varying the length of the segments is performed in steps, starting from a base signal length.

5. The method according to claim 4 wherein varying the length of the segments is increased in steps, starting from a minimum length.

6. The method according to claim 4 wherein the steps have a size proportional to the deviation of the inverse transform of the base signal from the electrical signal.

7. A method for the correction of measured value falsifications in invasive pressure measurements with a fluid-filled system, the method comprising:

passing measured pressure, as a pressure signal, via the fluid-filled system to an external pressure transducer;

converting the pressure signal into an electrical signal;

digitizing the electrical signal in an analog/digital converter;

feeding the digitized too signal analyzing and processing unit, which operates using digital Fourier analysis;

analyzing the digitized signal on a heartbeat-related basis;

combining the digitized signal analyzed on the heartbeat-related basis with prescribable correction data in a form of Fourier coefficients, with a fundamental frequency being determined by means of an autocorrelation function and a first derivative with respect to time of the autocorrelation function, such that the digital signal is corrected by the signal analyzing and processing unit, and passing the corrected signal to at least one of an output and evaluating unit.

8. The method according to claim 7, wherein the correction data are called up from a correction data record matrix of correction data records.

9. The method according to claim 8 wherein the correction data are called up as a correction data record vector.

10. The method according to claim 7 further comprising performing a phase and/or amplitude correction of the analyzed signal.

11. The method according to claim 10 wherein the phase correction of the analyzed signal takes place only at the points where the analyzed signal has an amplitude.

12. The method according to claim 8 further comprising performing an interpolation between the correction data records.

13. The method according to claim 8 wherein the correction data record matrix is determined by introducing the fluid-filled system into a device which can be subjected to pressure and the device is subjected to different medium pressures and frequencies, such that a reference pressure measurement is performed using a different measuring system and harmonic analysis is carried out.

14. The method according to claim 8 further comprising determining correction data records using a frequency grid for system excitation.

15. The method according to claim 14 wherein the frequency grid is based on a fundamental oscillation and harmonic oscillations.

16. The method according to claim 15 wherein the fundamental frequency lies between 0.2 Hz and 3 Hz.

17. The method according to claim 16 further comprising exciting a corresponding number of harmonic oscillations until a fixed upper limit is reached by equidistant intervals.

18. The method according to claim 17 wherein the upper limit is 40 Hz.

19. The method according to claim 9 further comprising multiplying repeatedly a pressure signal segment until a ratio which corresponds to a resolution of a correction data record is obtained between sampling rate and a length of a curve segment, in order to achieve a coincidence of spectral lines of the digitized signal to be corrected with those of the correction data record vector.

20. The method according to claim 19 further comprising:
    setting a next-smaller ratio between the sampling rate and the length of the curve segment; and
    assigning to the spectral lines of the correction data record by rounding up to a next corresponding line.

21. The method according to claim 13 further comprising:
    determining transmission characteristic of the fluid-filled system by means of white frequency noises; and
    performing a correction by means of deconvolution of an output signal with a transmission function.

22. The method according to claim 7 further comprising amplifying the electrical signal from the pressure transducer.

23. The method according to claim 7 further comprising supplying the pressure transducer with voltage by the signal analyzing and processing unit.

24. The method according to claim 7 wherein the fundamental frequency is determined by means of an autocorrelation function and the first derivative with respect to time of the autocorrelation function.

25. The method according to claim 19 wherein the fundamental frequency is determined by means of a combination of a distribution analysis of maxima of autocorrelation functions of varying length with analysis of minima and maxima of the curve segment.

26. The method according to claim 25 further comprising performing online determination of the fundamental frequency by repeating the autocorrelation functions with an increasing length, collecting all first maxima of the autocorrelation functions of the increasing length and determining a most frequently occurring maximum by means of a distribution analysis.

27. The method according to claim 7 further comprising determining the ECG signal delay time by performing a cross-correlation of the pressure signal and a patient's electrocardiogram (ECG).

28. The method according to claim 7 further comprising performing a system identification by means of a test signal response.

29. The method according to claim 28 wherein the system identification is performed automatically.

30. The method according to claim 28 or 29 further comprising performing a manual interaction in the system identification.

31. The method according to claim 28, further comprising performing a continuous measurement of medium pressure.

32. The method according to claim 28 further comprising generating a test signal by the pressure transducer.

33. The method according to claim 28 further comprising generating a test signal by a calibrator.

34. The method according to claim 7 further comprising adapting a pressure transducer for the fluid filled system.

35. The method according to claim 7 further comprising identifying of artifacts on a basis of system identification, harmonic base frequency and signal medium pressure.

36. The method according to claim 35 further comprising:
    performing an artifact identification and elimination by means of an autocorrelation function; and
    smoothing interference by an interpolation of measured values at a point of a spike.

37. The method according to claim 7 further comprising performing an analysis of the fundamental frequency, medium pressure and shape of the pressure signal by means of harmonic analysis.

38. The method according to claim 37 further comprising performing a correction taking into account higher harmonic fundamental oscillations.

39. The method according to claim 7 further comprising outputting an untransformed signal.

40. The method according to claim 7, further comprising performing a calibration of the system using a zero point calibration, a reference pressure measurement and/or a test signal.

41. The method according to claim 7 wherein the electrical signal is post-filtered and/or post-corrected.

42. The method according to claim 41 wherein the post-correction of the electrical signal is carried out on basis of a first derivative of the pressure signal with respect to time.

43. The method according to claim 42 wherein the post-filtering is carried out by means of a frequency and/or mean-value filter.

44. The method according to claim 7, further comprising performing an automatic adaptation to changes of resonant response as a result of pressure changes.

45. A device for the correction of measured value falsifications in invasive pressure measurements of a fluid-filled system, the device comprising:
    a pressure transducer converting recorded pressures into electrical signals;
    an analog/digital converter, connected to the pressure transducer, digitizing the electrical signals;

signal analyzing and processing unit connected to the analog/digital converter; and an output or evaluating unit connected to the signal analyzing and processing unit;

wherein the signal analyzing and processing unit has a means for carrying out a Fourier analysis, which breaks down the digitized signal into segments and subjects the segmented signals to a Fourier analysis, the segmented signals being capable of being combined with prescribable correction data in a form of Fourier coefficients and length of the segments being varied such that a minimal error occurs in the Fourier analysis.

46. The device according to claim 45 further comprising an interface designed as a digital/analog converter, amplifier and/or adaptor.

47. The device according to claim 45 or 46 wherein the signal analyzing and processing unit includes a memory and a correction data record matrix is stored in the memory of the signal analyzing and processing unit.

48. The device according to claim 45 further comprising a signal output for an uncorrected signal.

49. The device according to claim 45 further comprising a device measuring blood pressure fluctuations.

* * * * *